US009766252B2

(12) United States Patent
Kannan et al.

(10) Patent No.: US 9,766,252 B2
(45) Date of Patent: Sep. 19, 2017

(54) PEPTIDE WITH GOLD BINDING AND EGFR RECEPTOR AFFINITY AND SAME ATTACHED TO GOLD NANOSTRUCTURE

(71) Applicant: The Curators of the University of Missouri, Columbia, MO (US)

(72) Inventors: Raghuraman Kannan, Columbia, MO (US); Gerald Arthur, Rocheport, MO (US); Charles W. Caldwell, Jr., Columbia, MO (US); Charles Caldwell, Columbia, MO (US); Mripen Chanda, Columbia, MO (US); Ajit Zambre, Columbia, MO (US); Mythili Ramachandran, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 14/386,269

(22) PCT Filed: Mar. 13, 2013

(86) PCT No.: PCT/US2013/030923
§ 371 (c)(1),
(2) Date: Sep. 18, 2014

(87) PCT Pub. No.: WO2013/142200
PCT Pub. Date: Sep. 26, 2013

(65) Prior Publication Data
US 2016/0041188 A1 Feb. 11, 2016

Related U.S. Application Data

(60) Provisional application No. 61/685,679, filed on Mar. 22, 2012.

(51) Int. Cl.
| C07K 7/08 | (2006.01) |
| G01N 33/68 | (2006.01) |
| G01N 33/543 | (2006.01) |
| C07K 14/71 | (2006.01) |
| C07K 17/14 | (2006.01) |

(52) U.S. Cl.
CPC .......... *G01N 33/6872* (2013.01); *C07K 7/08* (2013.01); *C07K 14/71* (2013.01); *C07K 17/14* (2013.01); *G01N 33/54346* (2013.01); *G01N 2333/485* (2013.01)

(58) Field of Classification Search
None
See application file for complete search history.

(56) References Cited

U.S. PATENT DOCUMENTS

| 6,727,072 B2 | 4/2004 | Spaulding et al. |
| 2007/0009972 A1 | 1/2007 | Chao et al. |
| 2012/0040915 A1 | 2/2012 | Mukhopadhyay et al. |

FOREIGN PATENT DOCUMENTS

| JP | 2010007169 A | 1/2010 |
| WO | 2008000517 A2 | 1/2008 |

OTHER PUBLICATIONS

Vogel, C., et al, "Structure, function and evolution of multidomain proteins," Current Opinion in Structural Biology 2004, 14:208-216.*
Niidome, Takuro, et al., "PEG-modified gold nanorods with a stealth character for in vivo applications", Journal of Controlled Release, 114, (2006), pp. 343-347.
Supplementary European Search Report Dated Nov. 27, 2015.
Baslega, J., "Does Epidermal Growth Factor Receptor Status Predict Activity of Cetuximab in Colorectal Cancer Patients?", Nature Clinical Practice Oncology, 2, (2005), pp. 284-285.
Buckley, A.F., et al., "Comparison of the Dako EGFR pharmDx kit and Zymed EGFR Antibody for Assessment of EGFR Status in Colorectal Adenocarcinoma", Appl Immunohistochem Mol Morphol, 15, (2007), pp. 305-309.
Guo, et al., "Overexpression of SGLT1 and EGFR in Colorectal Cancer showing a Correlation with the Prognosis", Med Oncol, 28, (2011), pp. S197-S203.
Hirsch, F.R., et al., "Comparison of Antibodies and Cutoff Points to Predict Benefit From Gefitinib in a Phase 3 Placebo-Controlled Study in Advanced Nonsmall-Cell Lung Cancer", Cancer, 112, (2008), pp. 1114-1121.
Mendelsohn, J., et al., "Epidermal Growth Factor Receptor Targeting in Cancer", Semin Oncol, 33, (2006), pp. 369-385.
Penault-Llorca, F., et al., "Is there an Immunohistochemical Technique Definitively Valid in Epidermal Growth actor Receptor Assessment?", Oncol Rep, 16, (2006), pp. 1173-1179.
Pirker, R., et al., "EGFR Expression as a Predictor of Survival for First-Line Chemotherapy Plus Cetuximab in Patients with Advanced Non-small-cell Lung Cancer: Analysis of Data from the Phase 3 FLEX study", Lancet Oncol, 13, (2012), pp. 33-42.
Rivera, F., et al., "Cetuximab, its Clinical Use and future perspectives", Anticancer Drugs,19, (2008), pp. 99-113.
Tol, J., et al., "Monoclonal Antibodies in the Treatment of Metastatic Colorectal Cancer: a Review", Clin Ther, 32, (2010), pp. 437-453.
Vignot, S., et al., "Prognostic Value of EGFR in Colorectal Cancer", Bull Cancer, 92, (2005), pp. S13-S16.

(Continued)

*Primary Examiner* — Thomas S Heard
(74) *Attorney, Agent, or Firm* — Greer, Burns & Crain, Ltd.; Steven P. Fallon

(57) ABSTRACT

An embodiment of the invention is a peptide comprising four domains, wherein domain I consists of thioctyl or monocytl, domain II consists of 2 to 3 positively charged amino acids selected from the group consisting of lysine and arginine, domain III consists of a dimeric ethylene unit; and domain IV comprises the peptide with SEQ ID No. 1 or a sequence having at least 90% identity to SEQ ID No. I. The peptide is preferably attached to a gold nanostructure, preferably a gold nanorod to provide an EFGR kit. An EFGR detection kit of the invention employs a gold nanostructure attached to a peptide sequence, the peptide sequence includes a binding sequence with an affinity toward EGFR, a ligand bound to gold atoms of the nanorod, a positively charged amino acid that maintains activity of the binding sequence, and a unit that increases hydrophilicity of the peptide sequence.

10 Claims, 7 Drawing Sheets

(56) References Cited

OTHER PUBLICATIONS

Crow, Matthew, et al. "Molecular Imaging and Quantitative Measurement of Epidermal Growth Factor Receptor Expression in Live Cancer Cells Using Immunolabeled Gold Nanoparticles", American Journal of Roentgenology, vol. 192, No. 4, Apr. 2009, pp. 1021-1028.

Prajapati, Parima, M.,et al., "Gold Nanoparticles A new approach for cancer detection", Journal of Chemical and Pharmaceutical Research, vol. 2, No. 1, (2010), pp. 0975-7384.

* cited by examiner

PEPTIDE WITH GOLD BINDING AND EGFR RECEPTOR AFFINITY AND SAME ATTACHED TO GOLD NANOSTRUCTURE

PRIORITY CLAIM AND REFERENCE TO RELATED APPLICATION

The application claims priority under 35 U.S.C. §119 and applicable treaties from prior provisional application Ser. No. 61/685,679, which was filed on Mar. 22, 2012.

REFERENCE TO SEQUENCE LISTING

A sequence listing that has been submitted on electronic form and also duplicated on paper after the abstract is part of this specification.

FIELD

A field of the invention is epidermal growth factor receptor (EGFR) detection. An example application of the invention include is a kit for the detection of EGFR. Kits and methods of the invention can be used to screen patients for a number of anti-cancer therapies, e.g., cetuximab and panitumumab therapies.

BACKGROUND

The epidermal growth factor receptor (EGFR; HER1) is a cell surface receptor that regulates cell migration, adhesion, and proliferation. Overexpression of EGFR can be identified in many aggressive cancers such as colon, lung, and breast cancer as well as glioblastoma multiforme. EGFR is overexpressed in the cell membrane of a variety of malignant neoplasms, including colorectal, non-small cell lung carcinoma, head and neck carcinoma, and glioblastoma. EGFR has been identified as an oncogene, a gene that has the potential to cause cancer. Many targeted anticancer therapeutic approaches are aimed at the inhibition of EGFR. In order for the therapy to be effective, precise determination of the EGFR expression levels within the cell membrane is important, because only EGFR-dependent (EGFR positive) tumors respond to these therapeutic approaches.

EGFR is overexpressed in the cell membrane of a variety of malignant neoplasms, including colorectal adenocarcinoma, non-small cell lung carcinoma, head and neck carcinoma, and glioblastoma. See, Mendelsohn, J. & Baselga, J., "Epidermal Growth Factor Receptor Targeting in Cancer," Semin Oncol 33, 369-385 (2006); Pirker, R., et al., "EGFR Expression as a Predictor of Survival for First-Line Chemotherapy Plus Cetuximab in Patients with Advanced Non-small-cell Lung Cancer: Analysis of Data from the Phase 3 FLEX study," Lancet Oncol 13, 33-42 (2012). EGFR has been identified as an oncogene, a gene that has the potential to cause cancer. Many targeted anticancer therapeutic approaches are aimed at the inhibition of EGFR. See, e.g., Tol, J. & Punt, C. J., "Monoclonal Antibodies in the Treatment of Metastatic Colorectal Cancer: a Review," Clin Ther 32, 437-453 (2010). EGFR inhibitor cetuximab is currently used for treating colorectal carcinoma in humans. See, e.g., Rivera, F, et al. "Cetuximab, its Clinical Use and future perspectives," Anticancer Drugs 19, 99-113 (2008). For the therapy to be effective, precise determination of the EGFR expression levels within the cell membrane is important, because only EGFR-dependent (EGFR positive) tumors respond to these therapeutic approaches. Similarly, patients with tumors that do not express EGFR (EGFR negative) are more likely to be unaffected by the treatment. See, e.g., Vignot, S. and Spano, J., "Prognostic Value of EGFR in Colorectal Cancer. Bull Cancer 92, S13-16 (2005); Guo et al., "Overexpression of SGLT1 and EGFR in Colorectal Cancer showing a Correlation with the Prognosis," Med Oncol 28, S197-203 (2011).

Cetuximab is an IV administered drug and costs on the order of $30,000 for eight weeks of treatment per patient. For this reason, some insurance carriers have mandated that an EGFR diagnostic test be conducted for patients before selection of an appropriate therapeutic modality.

The Dako EGFR-pharmDx™ immunohistochemistry kit has been FDA-approved as an aid in identifying colorectal cancer patients that would benefit from treatment with cetuximab and panitumumab therapies. See, e.g., U.S. Pat. No. 6,727,072. This kit is used with a multi-step process to provide a visual signal that can be analyzed with a light microscope. The kit uses immunohistochemical staining procedure with a primary monoclonal mouse antibody that selectively binds to EGFR. Primary antibodies bound to tissue antigens are detected using a peroxidase labeled polymer that is conjugated with secondary anti-mouse immunoglobulin antibodies. Enzymatic conversion of a subsequently applied chromogen forms a visible reaction product at the site of the EGFR antigen. Specimens are then counterstained and coverslipped for interpretation with a light microscope. The optical results depend upon a produced chromogen, which can provide ambiguous signals. Testing procedures must ensure control cell line staining falls within an acceptable range that is neither too light nor too dark after checking different magnifications. Weak staining intensity of a cell line can result in false-negative tests. Excessive staining can result in false positive results. The staining and analysis procedure also requires careful examination of a region or a representative area and recognition and interpretation of possible artifacts. Careful monitoring of the positive indication percentage is required to ensure that the kit and method produce valid results. The effectiveness of the kit has been examined in various publications. See, Buckley, A. F. & Kakar, S., "Comparison of the Dako EGFR pharmDx kit and Zymed EGFR Antibody for Assessment of EGFR Status in Colorectal Adenocarcinoma," Appl Immunohistochem Mol Morphol 15, 305-309 (2007); Penault-Llorca, F., et al., "Is there an Immunohistochemical Technique Definitively Valid in Epidermal Growth. Factor Receptor Assessment?" Oncol Rep 16, 1173-1179 (2006). In practical experience, there are variations of the results obtained by different laboratories. Dako provides procedures intended to produce more consistent results. The kit's accuracy has been demonstrated to be about 51%. This could be caused by the testing procedures, or could be related to the fact that tissue fixation methodology and the quality of antibody affect results. Studies have estimated that the EGFR expression levels varied from 4% to 72% depending on the kit used. Baselga J., "Does Epidermal Growth Factor Receptor Status Predict Activity of Cetuximab in Colorectal Cancer Patients? Nature Clinical Practice Oncology 2, 284-285 (2005); Hirsch, F. R. et al., "Epidermal Growth Factor Receptor Immunohistochemistry,". Cancer 112, 1114-1121 (2008). Another drawback is the time required for test turn-around, which is typically 24-48 hours.

Another antibody based kit was developed by Zymed (subsequently acquired by Invitrogen), and was called the EGFr Kit (clone 31G7). This test had an accuracy that was better (~62%) than the Dako EGFR-pharmDx™ kit. However, this accuracy is still low. In addition, as another antibody based kit, the kit suffered from laboratory variation as well as sensitivity to tissue fixation methodology and quality of antibody clone. It is not believed that this kit is currently available.

SUMMARY OF THE INVENTION

An embodiment of the invention is a peptide comprising four domains, wherein domain I consists of thioctyl or monocytl, domain II consists of 2 to 3 positively charged amino acids selected from the group consisting of lysine and arginine, domain III consists of a dimeric ethylene unit; and domain IV comprises the peptide with SEQ ID No. 1 or a sequence having at least 90% identity to SEQ ID No. 1. The peptide is preferably attached to a gold nanostructure, and particularly a gold nanorod to provide an EFGR kit.

An EFGR detection kit of the invention employs a gold nanostructure attached to a peptide sequence, the peptide sequence includes a binding sequence with an affinity toward EGFR, a ligand bound to gold atoms of the nanostructure, a positively charged amino acid that maintains activity of the binding sequence, and a unit that increases hydrophilicity of the peptide sequence.

DETAILED DESCRIPTION OF THE PREFERRED EMBODIMENTS

Figures 1A, 1B:
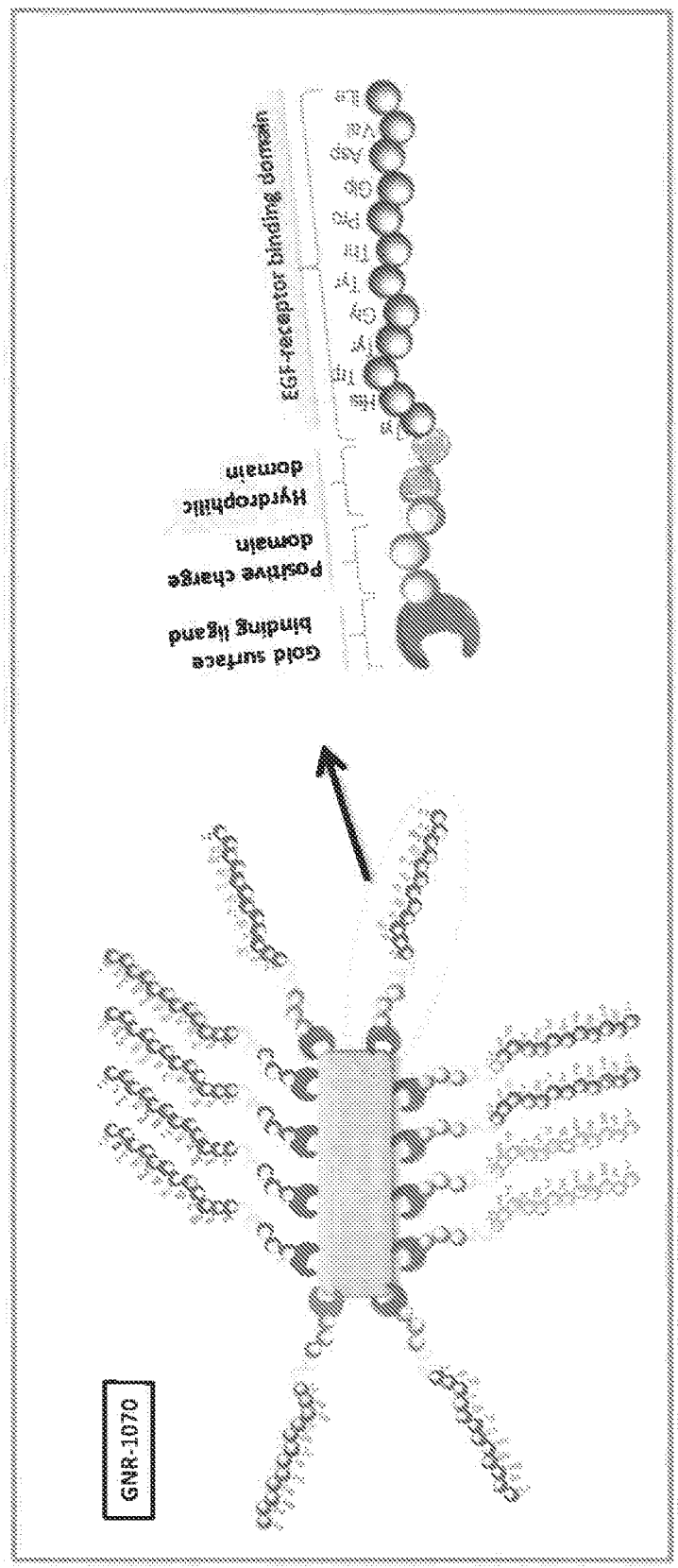
FIG. 1A schematically illustrates a gold nanorod with a plurality of peptide chains having an affinity for EFG receptors attached in accordance with an EFGR detection kit of the invention.
FIG. 1B illustrates a particular preferred embodiment four domain gold nanorod (GNR) kit component referred to as GNR-1070.

A preferred embodiment of the invention is a peptide comprising four domains, wherein domain I consists of thioctyl or monocytl, domain II consists of 2 to 3 positively charged amino acids selected from the group consisting of lysine and arginine, domain III consists of a dimeric ethylene unit; and domain IV comprises the peptide with SEQ ID No. 1 or a sequence having at least 90% identity to SEQ ID No. 1. The peptide is preferably attached to a gold nanostructure, and most preferably a gold nanorod. Peptides attached to a gold nanostructure forms a preferred embodiment EFGR detection kit. The kit provides strong optical signaling of EFGR detection.

Another preferred embodiment of the invention is an EGFR detection kit. The kit identifies EGFR-expressing cells in a tissue sample. It stains the EGFR-expressing cells with a bright yellow signal to readily distinguish them from the normal, healthy cells present in the tissue. An EFGR detection kit of the invention employs a gold nanostructure attached to a peptide sequence, the peptide sequence includes a binding sequence with an affinity toward EGFR, a ligand bound to gold atoms of the nanostructure, a positively charged amino acid that maintains activity of the binding sequence, and a unit that increases hydrophilicity of the peptide sequence. The EFGR detection kit can provide a method to detect and quantify EGFR expression in human tissues utilizing dark-field microscopy. A detection kit of the invention can be used in a simple two-step detection procedure. A kit according to a preferred embodiment of the invention also includes EGFR positive and negative cells that are used during testing as positive and negative controls.

Preferred embodiments of the invention use gold nanorods as the gold nanostructure. Experiments have demonstrated strong signals from gold nanorod based EFGR detection kits of the invention. The nanorods provide a strong signal. Gold nanospheres can be used, and can be obtained from conventional gold nanostructure fabrication processes. The peptide sequence attaches to gold molecules, and therefore other shapes of gold nanostructures can also be used.

Preferred embodiments of the invention will now be discussed with respect to the drawings. The drawings may include schematic representations, which will be understood by artisans in view of the general knowledge in the art and the description that follows. Features may be exaggerated in the drawings for emphasis, and features may not be to scale.

FIGS. 1A and 1B show a gold nanorod 10 a peptide sequence 12. A preferred embodiment peptide sequence 1070 (Thioctyl-KK-PEG2-YHWYGYTPQNVI)(wherein YHWYGYTPQNVI is SEQ ID No 1) is specially designed to have a positive surface potential and charge, and is also highly hydrophilic so as to recognize and adhere to EGF receptors under biological conditions. The peptide sequence 12 in FIGS. 1A and 1B consists of four independent domains integrated into the sequence. Domain-I contains thioctyl that can irreversibly bind to the gold atoms on the surface of nanorods. Monothiol provides less stability of attachment than thioctyl, but can also be used as a binder. Domain 41 contains positively charged amino acids purposely chosen in the sequence for retaining the biological activity of the peptide sequence, and serves to increase irreversible adsorption to the surface of the receptors. FIG. 1B shows three lysine molecules. Two molecules are preferred. More than three molecules is not acceptable. More than two decreases the specificity of the peptide towards receptors, and more than 3 reduces specificity to too great a degree while also posing synthetic difficulties. Arginine can be substituted for lysine. Domain-III contains a dimeric ethylene unit that increases the overall hydrophilicity of the peptide sequence. Domain-IV contains a 12-amino acid receptor binding sequence (SEQ ID No 1 or a sequence having at least 90% identify to SEQ ID No 1) that has high affinity toward EGF receptors.

SEQ ID No. 1 (Tyr His Trp Tyr Gly Tyr Thr Pro Gln Asn Val Ile)

In some embodiments, domain IV is a peptide with SEQ ID No 1 which recognizes and binds to an EGF receptor. In other embodiments, any derivative peptide with at least 90% amino acid sequence identity to the peptide with SEQ ID No I can be used. Such derivative peptides include, but are not limited to, peptides in which at least one amino acid in SEQ ID No 1 is substituted for another amino acid. Any of amino acids, including modified amino acids, can be used to substitute at least one amino acid in SEQ ID No 1. In some embodiments, a derivative peptide possesses the affinity to an EGF receptor similar to that of the peptide with SEQ ID NO. 1. Additional derivative peptides may include those in which some amino acids in SEQ ID No 1 are deleted or those in which additional amino acids are added to SEQ ID No 1.

Two Step Assay Process

Figure 2:
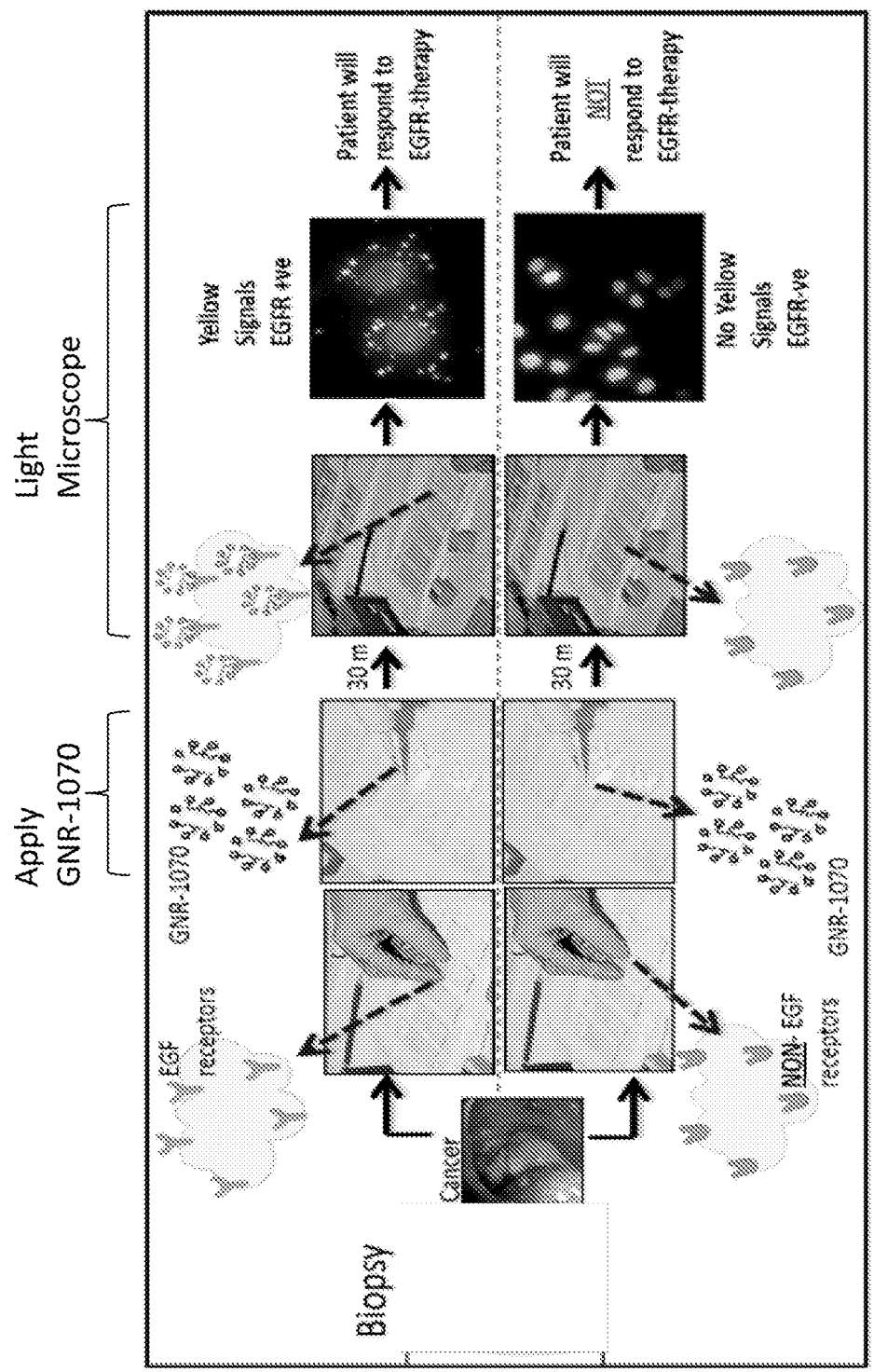
FIG. 2 indicates a method of the invention for testing with an EGFR kit of the invention.

Experiments demonstrated that a simple two step process can be used for the detection of EGFR using a kit of the present invention. FIG. 2 shows the basic process, which consists of application of a kit of the invention to a tissue sample and examination with a light microscope. A preliminary step is preparation of a biopsy tissue sample. Details of a preferred assay process are included in the Experimental Data.

Experimental Data

Sensitivity

Testing showed that a kit of the invention is sensitive in identifying receptors present in the surface membrane of a single human cell. The kit of the invention was tested with EGFR-positive fixed cells and EGFR-negative fixed cells. Six positive cell lines and two negative cell lines were tested. Data obtained were consistent. A single EGFR-positive fixed cell showed a clear yellow signal on the outer rim of the cell that corresponds to the selective accumulation of the kit component, referred to as gold nanorod-1070 (GNR-1070) on the EGF receptors on the surface. In contrast, EGFR-negative cells treated with GNR-1070 show no characteristic yellow signals on the cell surface.

Results obtained with GNR-1070 and the testing method of the invention were compared to Dako EGFR-pharmDx™ and the EGFr Kit (clone 31G7). The GNR-1070 provides a significantly higher signal intensity (brightness) when bound to the EGF receptor than does the Dako method and kit. The gold nanorod portion of GNR-1070 provides a strong, visually identifiable signal in the presence of fewer numbers of EGF receptors than can be detected with the Dako kit. In some cases, the increased brightness permits the identification of even single positive cells.

Tissue Samples—EGFR Expression Testing

The EGFR binding ability of GNR-1070 in human tissues was evaluated for four tissue samples: adenocarcinoma of colon and lung, glioblastoma and normal lung tissue. As a first step, EGFR expressions in these tissues were determined using conventional reverse transcriptase PCR techniques. Based on this data, EGFR densities in the tissues follow this order: colon cancer>lung cancer>glioblastoma. Normal human tissue showed no EGFR expression, and served as a negative control for the studies. The yellow signal intensity produced with GNR-1070 testing corresponded well with EGFR-expression in the tumor tissues and follows the same order as obtained by PCR techniques. The results demonstrated that GNR-1070 can selectively stain EGFR in tissues and that GNR-1070 is suitable for quantifying EGF receptors on the tissue surface. Brightness and qualitative observations were used to quantify with a pathologist assigning values as a logists as +1, +2 or +3 scale.

Comparative Study

The first set of experiments involved treatment of EGFR +ve and EGFR-ve cells supplied with the Dako kit with the present GNR-1070 or EGFR-PharmDx and monitored by microscopic techniques. The specified procedures in the manual for the Daka kit were followed. EGFR-PharmDx stains EGF receptors as brown signals; whereas, GNR-1070 stains as bright yellow signals. The brown signals corresponded to EGFR in human colorectal tumor cells (HT-29). Similarly, the yellow signals indicated EGF receptors. "CAMA-1"-EGFR-ve cell lines showed no staining by both the assays. These results showed that GNR-1070 provides a kit that can duplicate the Dako kit result, but is more user friendly, requiring only two steps after tissue and slide preparation.

Tissue Staining Protocol for GNR-1070

The following is an example preferred tissue stating procedure: 1. Thaw slide if frozen or dewax slide if kept in paraffin. Dry slide when finished. 2. Block slide for 15 minutes with a buffer solution of 1% BSA in 1×PBS 3. Wash slide thoroughly with 1×PBS. Tap excess PBS off of slide and dry. 4. Treat tissue sample with GNR-1070 for 1 hour, making sure to cover entire tissue area. 5. Wash and dry slide with 1×PBS as in step 3. 6. Add staining agent to tissue if desired and coverslip the slide for imaging.

Importantly, the signal provided by the present GNR-1070 kit was much less ambiguous. This was tested in clinical applications. Human colorectal tumor microarray tissue was used for these studies. As the microarray sections are obtained from patients' tumor tissue blocks, the tissue morphology is minimally different from one microarray to another. This morphologic similarity enabled us to compare the same tissue with two different techniques. In our study, we treated one set of microarray tissues with the Dako kit and the other set with the present assay based upon GNR-1070. Each comparison study provided data equivalent to testing 198 individual human tissue samples (99 tissue sections per assay). Two sets of comparative studies provided the equivalent of 396 individual human tissue samples. Intensity grading was provided by a board certified pathologist. The result was that the assay based upon the present GNR-1070 stained with high signal intensity (3+) and membrane affinity in tumor regions that were identified as weak (1+) by Dako's EGFR kit.

Synthesis of GNR-1070

GNR-1070 as shown in FIG. 1B was synthesized as follows with standard Fmoc chemistry. The Fmoc-amino acid derivatives and Fmoc-Ile-Wang resin were used and included Fmoc-PEG2-OH.

Elongation cycle for peptide synthesis: Deprotection: Piperdine/DMF solution 20% (10 ml/g resin) was added to the peptide resin and stirred for 20 min and the solution was drained out. This was repeated again and further washed 6 times with DMF. The Kaiser test was performed and found to be positive. Coupling: Dissolved 4 equivalents Fmoc-AA in DMF and added to the Ile-Wang resin. Three equivalents HBTU and 4 equivalents DIPEA were added. The reaction was stirred for ~60 mins and further the resin was washed 6 times with DMF. The Kaiser test was performed and found to be negative. Repeating cycle of deprotection/coupling/deprotection until last Fmoc group of Fmoc-Lys(Boc)-peptide resin was removed. Four equivalents of thioctic acid and DIC were added in DMF and the reaction mixture was stirred for ~40 min. The resin was washed with DMF six times. The Kaiser test was performed and found to be negative. The completed resin was further washed by Isopropanol (2 times), DMF (4 times), and ether (2 times). The synthesized resin was dried under the vacuum.

Figure 3:
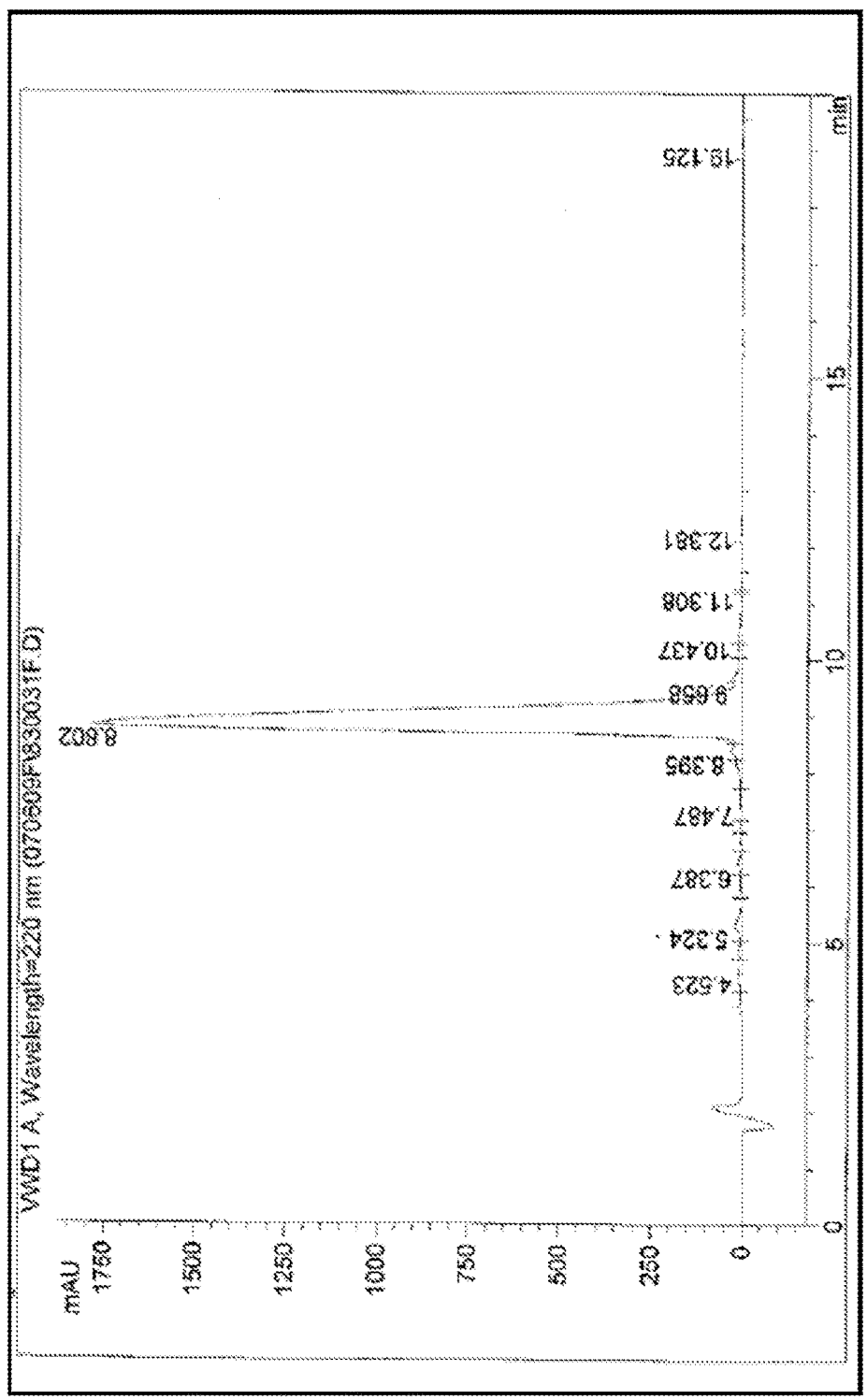
FIG. 3 shows the HPLC testing results of example 1070 peptide.
Figure 4:
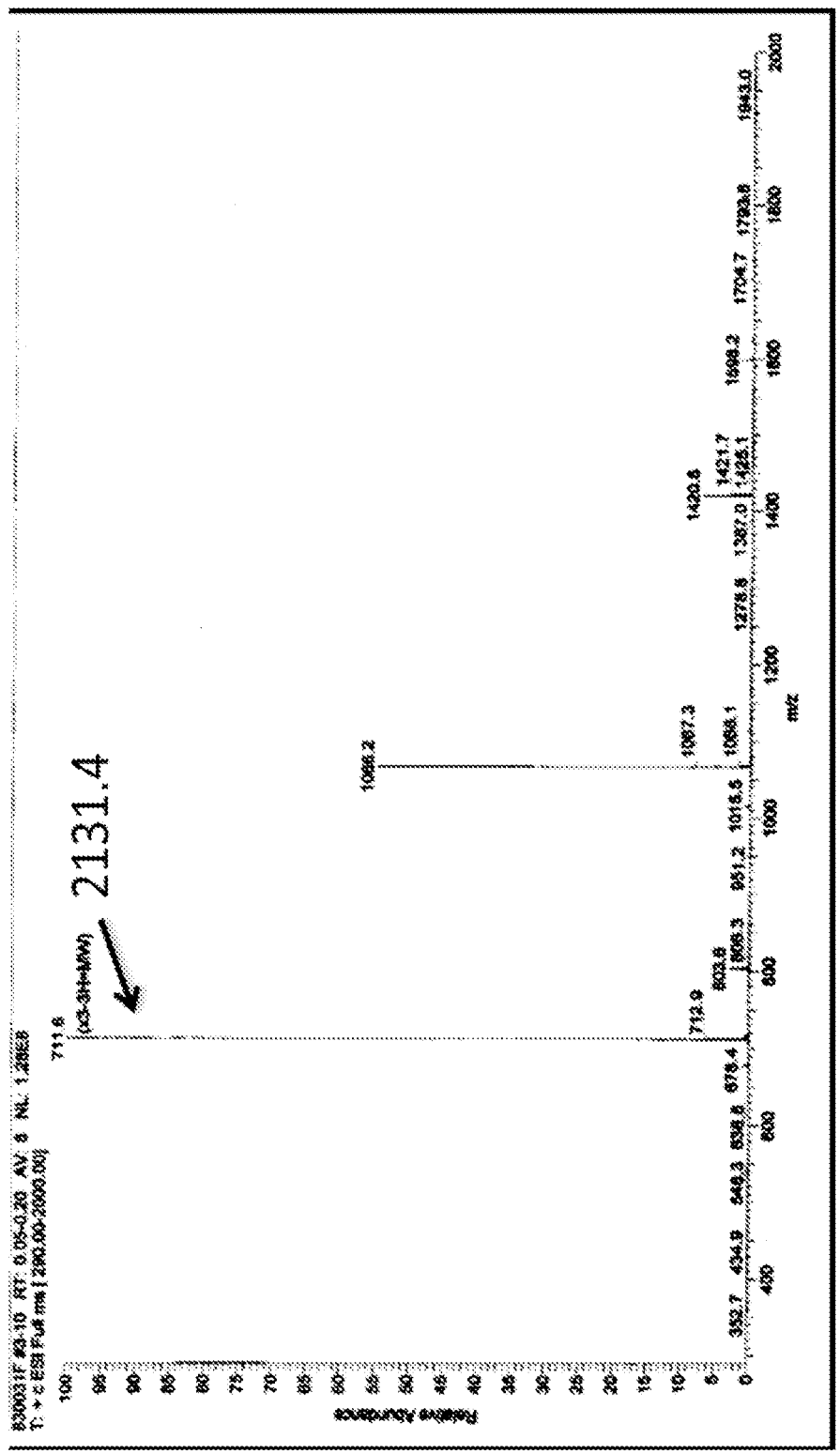
FIG. 4 shows the mass spectrum measurements of example 1070 peptide.

TFA Cleavage:

Used the ratio of 10 ml/g resin. TFA containing 20% Anisol was added to the peptide resin and stirred under 0° C. for 150 min. The resin was filtered off and the TFA cocktail solution was collected. The dry cold ether was added to the cocktail solution and off-white precipitated crude peptide was collected by simple filtration. The crude was washed with cold ether again and dried it completely. FIG. 3 shows the HPLC testing results of example 1070 peptide. FIG. 4 shows the mass spectrum measurements of example 1070 peptide.

Gold nanorods (GNR) of aspect ratio 3.4 were prepared using an established seed-mediated growth method. All solutions were made in fresh deionized water (DI $H_2O$). A seed solution was prepared by making a 10 mL solution of 0.1M Cetyltrimethylammonium Bromide (CTAB). The CTAB solution was lightly heated until the CTAB had dissolved, giving a clear solution. 250 μL of a 0.01M solution of chlorauric acid (HAuCl$_4$) was then added to the CTAB solution while stirring. Immediately after addition of chlorauric acid, 650 μL of ice-cold 0.01M sodium borohydride (NaBH$_4$) was added to the solution, which changed color from gold to light brown. The seed solution was then left to stir for 5 minutes. While the seed solution stirred, 500 mL of growth solution was then prepared. The first step was to make 250 mL of a 0.1M CTAB solution, and then heat until the CTAB had dissolved as had been done with the seed solution. 250 mL of 0.001M chlorauric acid was then added to this CTAB solution and stirred lightly by hand. 10 mL of 0.0043M silver nitrate (AgNO$_3$) was added to the solution and again stirred gently by hand. 4 mL of 0.1M ascorbic acid was then added, and the solution was stirred very gently until the solution had turned from gold-orange to clear. This completed the growth solution. 0.5 mL of the seed solution was then added in to the growth solution. The solution was not touched after this point due to the delicate nature of the synthesis. Minutes later the solution turned from clear to purple, indicating the formation of GNR.

The GNR solution was left alone for 24 hours, and then washed of CTAB. The GNR solution was twice filtered through filter paper to remove excess CTAB. The filtered solution was left again overnight to allow more CTAB to aggregate. The filter process was then repeated. To further remove excess CTAB, the solution was then centrifuged at 16,000 RPM for 10 minutes at 25 C. The supernatant was removed and replaced with fresh DI H$_2$O. The centrifuging step was then repeated.

Figure 5:
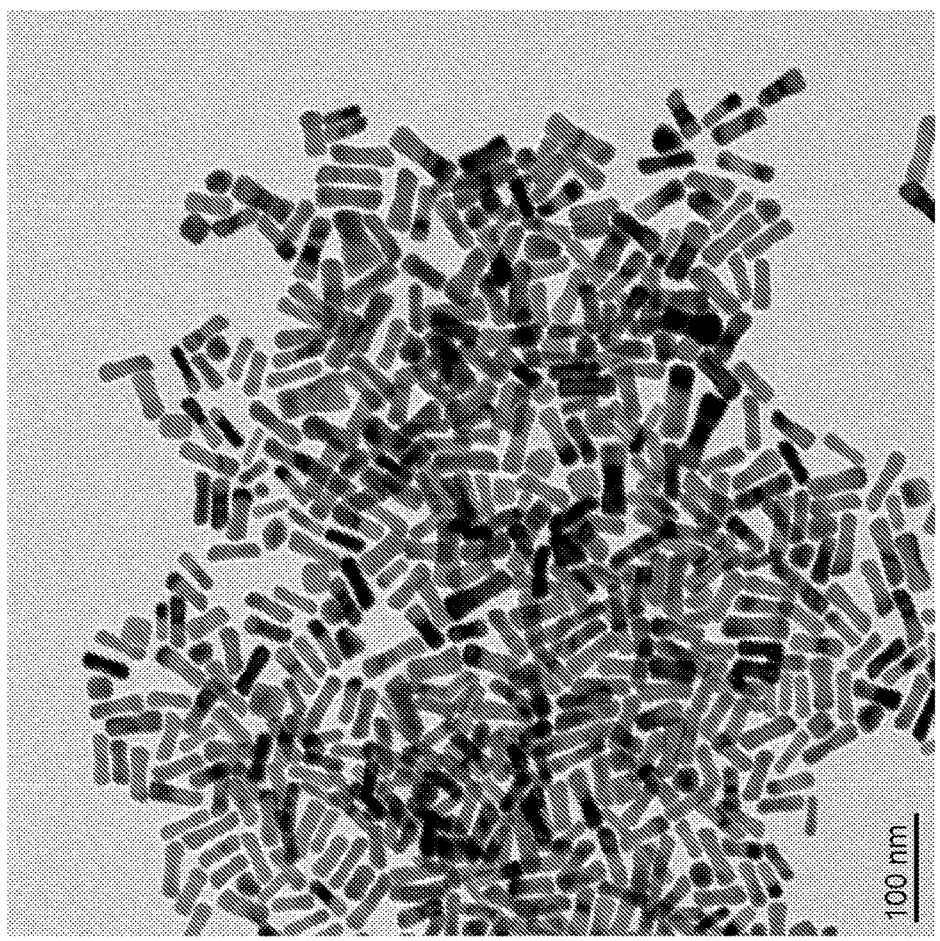
FIG. 5 is a TEM image of GNR-1070.
Figure 6:
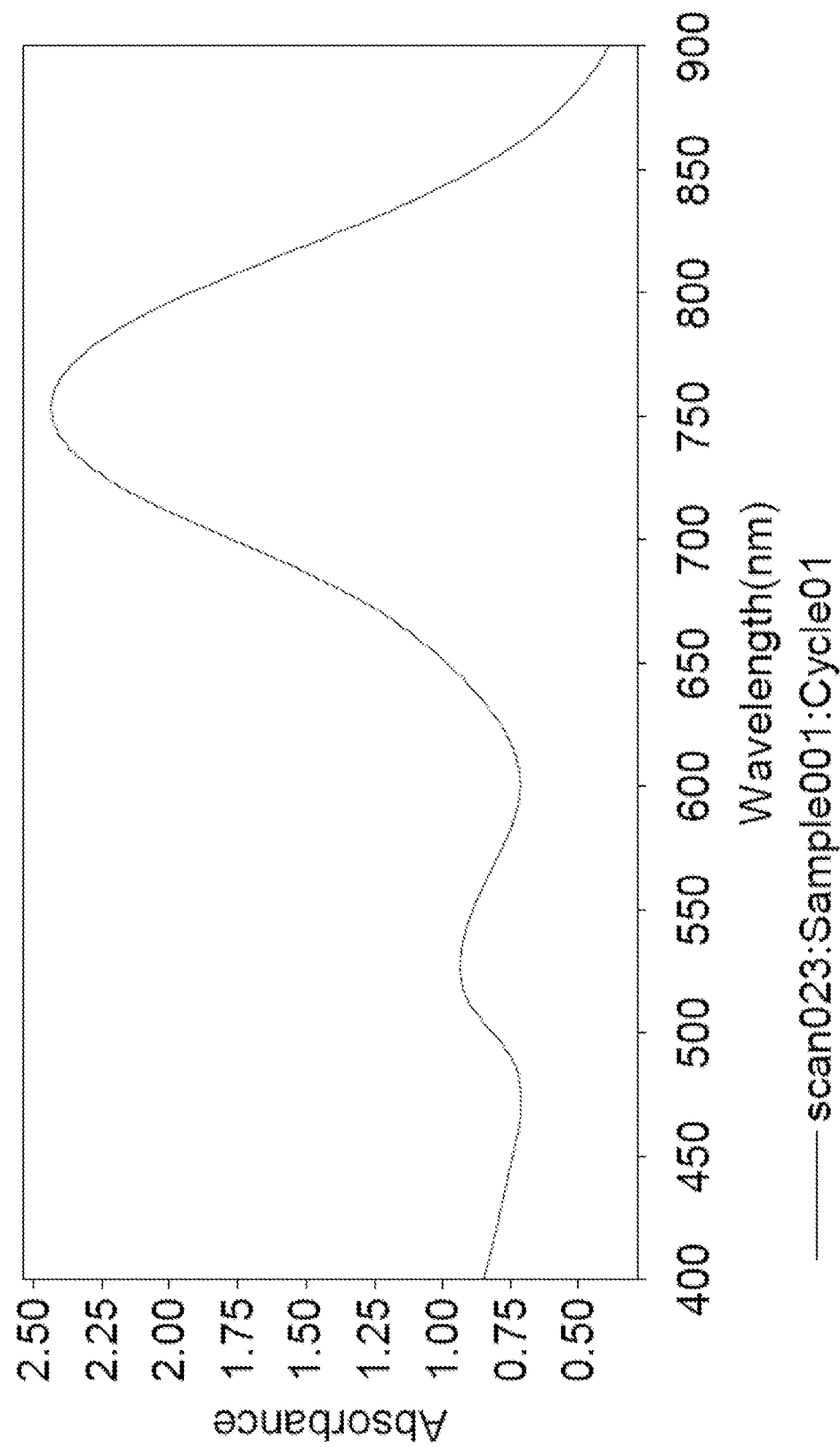
FIG. 6 plots optical response of GNR-1070.
Figure 7:
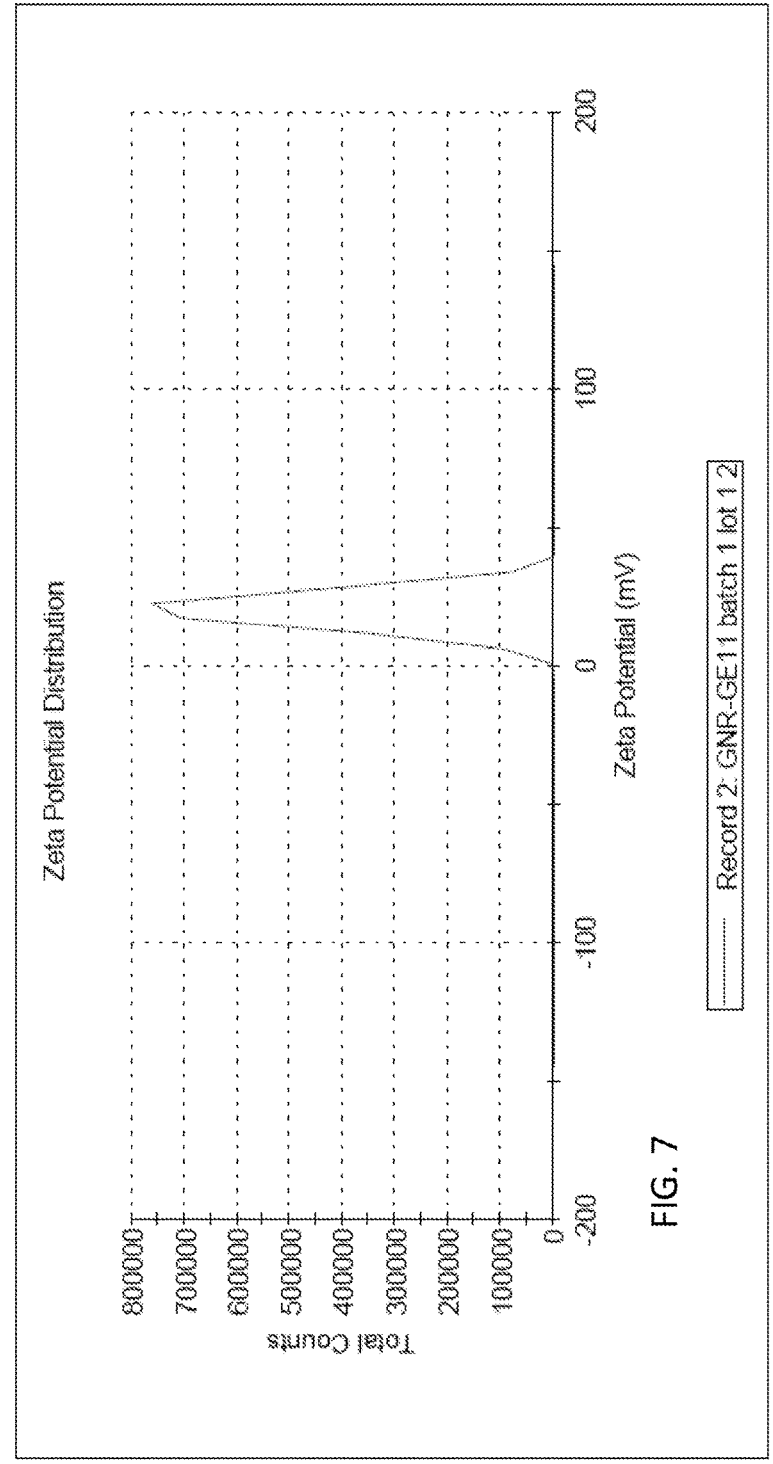
FIG. 7 plots zeta potential distribution of GNR-1070 solution.

In order to attach the 1070 peptide, a 750 dalton polyethylene glycol (PEG$_{750}$) linker modified with thiol was attached to the 1070 peptide. A solution of PEG$_{750}$ in DI H$_2$O was prepared using a molar ratio of 1:2 (GNR:PEG-750). A solution of 1070 peptide in DI H$_2$O was then added to the PEG solution at a molar ratio of 1:1 (GNR:1070 peptide). This PEG-1070 solution was mixed at RT then left for 15 minutes. After the 15 minutes, the PEG-1070 solution was then added to the GNR solution while stirring and left for 2 hours. The same washing protocol as with GNR-CTAB was followed after the 2 hour period. FIG. 5 is a TEM image of GNR-1070. FIG. 6 shows the absorbance as a function of wavelength. There is a strong absorbance band from ~725 nm to ~825 nm, with a peak near 750 nm. This forms a preferred range for light microscopy detection and will provide the strongest optical response. FIG. 7 is a plot of the zeta potential distribution of GNR 1070 solution.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A peptide comprising four domains, wherein domain I consists of thioctyl or monothiol, domain II consists of 2 to 3 positively charged amino acids selected from the group consisting of lysine and arginine, domain III consists of a dimeric ethylene unit; and domain IV comprises the peptide with SEQ ID No. 1.

2. The peptide of claim 1, wherein domain I consists of thioctyl.

3. The peptide of claim 2, wherein domain II consists of 2 molecules of lysine.

4. The peptide of claim 1, attached to a gold nanostructure.

5. The peptide of claim 4, wherein the gold nanostructure comprises a gold nanorod.

6. An epidermal growth factor receptor (EGFR) detection kit comprising a solution of peptides attached to the gold nanorod according to claim 5.

7. An epidermal growth factor receptor (EGFR) detection kit comprising a solution of peptides attached to gold nanorods according to claim 4.

8. An epidermal growth factor receptor (EGFR) detection kit comprising: a gold nanostructure attached to a peptide comprising four domains, wherein domain I consists of thioctyl or monothiol, domain II consists of 2 to 3 positively charged amino acids selected from the group consisting of lysine and arginine, domain III consists of a dimeric ethylene unit and domain IV comprises the peptide with SEQ ID No. 1.

9. The EGFR detection kit of claim 8, wherein the positively charged amino acids consists of 2 or 3 molecules of lysine.

10. An epidermal growth factor receptor (EGFR) detection kit comprising a solution of peptides attached to the gold nanostructure according to claim 4.

* * * * *

SEQUENCE LISTING

```
<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Synthetic peptide

<400> SEQUENCE: 1

Tyr His Trp Tyr Gly Tyr Thr Pro Gln Asn Val Ile
1               5                   10
```